United States Patent [19]
Papazoglou

[11] Patent Number: 6,098,630
[45] Date of Patent: *Aug. 8, 2000

[54] MULTIPLE DIAMETER EXPANDABLE GRAFT FOR BLOOD VESSEL AND METHOD FOR DEPLOYING THE SAME

[75] Inventor: Konstantinos Papazoglou, Phoenix, Ariz.

[73] Assignee: Endomed Inc., Phoenix, Ariz.

[*] Notice: This patent issued on a continued prosecution application filed under 37 CFR 1.53(d), and is subject to the twenty year patent term provisions of 35 U.S.C. 154(a)(2).

[21] Appl. No.: 08/885,626

[22] Filed: Jun. 30, 1997

Related U.S. Application Data

[63] Continuation of application No. 08/579,054, Dec. 21, 1995, abandoned, which is a continuation of application No. 08/258,728, Jun. 13, 1994, abandoned.

[51] Int. Cl.$^7$ ................................................. A61B 19/00
[52] U.S. Cl. ............................................... 128/898; 623/1
[58] Field of Search .................................. 623/1, 11, 12; 604/7–10, 175; 606/191–198; 600/29–31; 128/898

[56] References Cited

U.S. PATENT DOCUMENTS

| | | |
|---|---|---|
| 3,008,187 | 1/1961 | Slade . |
| 4,110,392 | 8/1978 | Yamazaki . |
| 4,250,138 | 2/1981 | Okita . |
| 4,441,215 | 4/1984 | Kaster ........................................ 623/12 |
| 4,482,516 | 11/1984 | Bowman et al. . |
| 4,733,665 | 3/1988 | Palmaz ........................................ 623/1 |
| 4,743,251 | 5/1988 | Barra . |
| 4,776,337 | 10/1988 | Palmaz . |
| 4,856,516 | 8/1989 | Hillstead . |
| 4,922,905 | 5/1990 | Strecker . |
| 4,955,859 | 9/1990 | Zilber . |
| 4,994,071 | 2/1991 | MacGregor ............................. 606/192 |
| 5,061,275 | 10/1991 | Wallsten et al. . |
| 5,061,276 | 10/1991 | Tu et al. . |
| 5,071,609 | 12/1991 | Tu et al. . |
| 5,078,726 | 1/1992 | Kreamer . |
| 5,108,424 | 4/1992 | Hoffman, Jr. et al. . |
| 5,122,154 | 6/1992 | Rhodes . |
| 5,123,917 | 6/1992 | Lee . |
| 5,217,483 | 6/1993 | Tower . |
| 5,219,355 | 6/1993 | Parodi et al. . |
| 5,258,020 | 11/1993 | Froix .......................................... 623/1 |
| 5,316,023 | 5/1994 | Palmaz et al. .......................... 128/898 |
| 5,360,443 | 11/1994 | Barone et al. ............................. 623/1 |
| 5,366,504 | 11/1994 | Andersen et al. . |
| 5,383,928 | 1/1995 | Scott et al. . |
| 5,425,765 | 6/1995 | Tiefenbrun et al. . |
| 5,667,486 | 9/1997 | Mikulich et al. ........................... 604/8 |
| 5,693,087 | 12/1997 | Parodi ........................................ 623/1 |

FOREIGN PATENT DOCUMENTS

| | | |
|---|---|---|
| 0 267 719 A2 | 11/1987 | European Pat. Off. . |
| 0 269 449 A2 | 11/1987 | European Pat. Off. . |
| 0 461 791 A1 | 6/1991 | European Pat. Off. . |
| 0 551 179 A1 | 1/1993 | European Pat. Off. . |
| WO 91/00712 | 1/1991 | WIPO . |
| WO 91/12779 | 9/1991 | WIPO . |
| WO 94/01056 | 1/1994 | WIPO . |
| WO 94/12136 | 6/1994 | WIPO . |
| WO 94/13224 | 6/1994 | WIPO . |

OTHER PUBLICATIONS

Palmaz, "Uses of Balloon Expandable Stents in Combination with PTFE" W.B. Saunders Company, Ltd., pp. 36–42, 1994.

*Primary Examiner*—John G. Weiss
*Assistant Examiner*—Dennis Ruhl
*Attorney, Agent, or Firm*—Michael I. Rackman; Tiberiu Weisz

[57] ABSTRACT

An expandable blood vessel graft facilitates the rapid and secure insertion of the graft in an blood vessel. The graft includes a first radially preexpanded portion and a second portion. The first portion is connected to the second portion. The second portion has a diameter less than the diameter of the first preexpanded portion.

6 Claims, 8 Drawing Sheets

MULTIPLE DIAMETER EXPANDABLE GRAFT FOR BLOOD VESSEL AND METHOD FOR DEPLOYING THE SAME

This is a continuation of U.S. Ser. No. 08/579,054, filed on Dec. 21, 1995, now abandoned; which is also a continuation of U.S. Ser. No. 08/258,728, filed on Jun. 13, 1994, now abandoned.

This invention relates to grafts.

More particularly, the invention relates to grafts for the blood vessels of animals.

In a further respect, the invention relates to expandable blood vessel grafts which facilitate the rapid and secure insertion of the grafts in the blood vessels.

In another respect, the invention relates to expandable blood vessel grafts which can be inserted at the bifurcation of a blood vessel.

The use of grafts in the blood vessels of human beings and other animals is well known in the art. However, several disadvantages are associated with prior art grafts. First, the time required to insert a graft can be substantial, particularly when an expandable graft is utilized which requires that an angioplasty balloon be inflated at several positions along the length of the graft in order to properly expand the graft. Second, the insertion of grafts near a bifurcation of a blood vessel, for example the aortic arterial bifurcation, is difficult.

Accordingly, it would be highly desirable to provide an improved blood vessel graft which would facilitate the rapid deployment of the graft in a blood vessel and which would facilitate the use of the graft at the bifurcation of a blood vessel.

SUMMARY OF THE INVENTION

Therefore, it is a principal object of the invention to provide an improved graft.

A further object of the invention is to provide an improved expandable blood vessel graft which facilitates the deployment of the graft in a blood vessel when the graft requires expansion at several points along the length of the graft.

Another object of the invention is to provide an improved blood vessel graft and method for inserting the graft at the bifurcation of a blood vessel.

BRIEF DESCRIPTION OF THE DRAWING

These and other, further and more specific objects and advantages of the invention will be apparent to those skilled in the art from the following detailed description thereof, taken in conjunction with the drawings, in which.

DETAILED DESCRIPTION OF THE INVENTION

Briefly, in accordance with the invention, I provide a graft for carrying blood. The graft includes a first portion having a diameter; and, a second portion connected to said first portion and having a diameter less than the diameter of said first expanded portion. The second portion is expandable with a balloon after the second, along with the first, portion is inserted in a blood vessel in the body of an animal.

In another embodiment of the invention, I provide a graft for carrying blood. The graft includes a first portion having a diameter; and, a second portion connected to said first portion and having an original diameter. The second portion is expandable with a balloon to a diameter greater than the original diameter after the second portion is inserted in a blood vessel in the body of an animal.

In a further embodiment of the invention, I provide a method for inserting in the body of an animal a graft for carrying blood. The method includes the steps of providing a graft including a first portion having a diameter, and a second portion connected to the first portion and having a diameter less than the diameter of the first portion, the second portion being expandable with a balloon after the second portion is inserted in a blood vessel in the body of an animal; inserting the second portion in the blood vessel of an animal; and, expanding the second portion with a balloon.

In still another embodiment of the invention, I provide a method for inserting in a human being a graft which extends into the aortic blood vessel bifurcation. The method includes the step of providing a graft. The graft includes a center portion having a pair of ends and a diameter; a first expandable portion connected to one end of the center portion; a first expandable leg connected to the other end of the center portion; and, a second expandable leg connected to the other end of said center portion. A portion of one end of a first length of suture is inserted through one side of the groin of the patient, through one iliac artery, through the other iliac artery, and out the other side of the groin of the patient such that the other end of said suture extends out through said one side of the groin. A portion of the suture extending out the other side of the groin of the patient is attached to the second expandable leg of the graft. A second length of suture is attached to the first expandable leg. The graft is inserted into the aorta through said other side of the groin such that the first and second expandable legs move through the aorta toward the patient's heart and past the junction of iliac arteries. The first and second lengths of suture are gently drawn in a direction out from the patient's body to move the graft away from the patient's heart such that the first and second expandable legs are each pulled down into one of the iliac arteries. The first expandable portion of the graft is expanded with a stent to secure the graft in place in the aorta.

Figure 1:
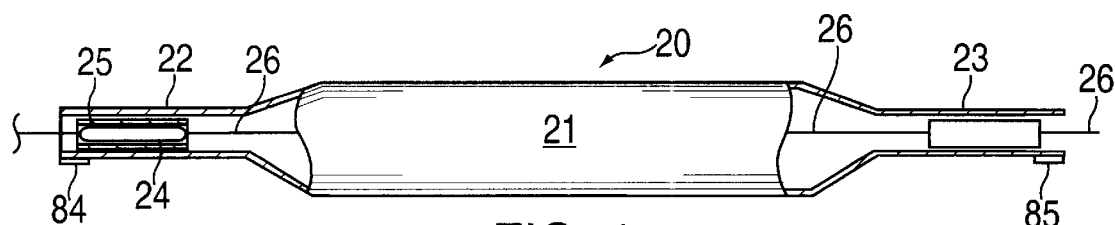
FIG. 1 is a side section view illustrating a blood vessel graft constructed in accordance with the principles of the invention.

Turning now to the drawings, which depict the presently preferred embodiments of the invention for the purpose of illustrating the practice thereof, and not by way of limitation of the scope of the invention, and in which like reference characters refer to corresponding elements throughout the several views, FIG. 1 illustrates a graft 20 constructed in accordance with the invention. In the graft 20 of FIG. 1, the diameter of center portion 21 is greater than the diameter of the proximal portion 22 and distal portion 23. The graft 20 is presently preferably made by taking a length of material like thin, pliable, expandable polytetrafluoroethylene (PTFE) tubing and expanding an intermediate section of the tubing to form center portion 21 while not expanding the proximal portion 22 and distal portion 23. Fabricating graft 20 from a thin, pliable, readily foldable material is preferred because one primary application of the graft requires that the graft be folded into a small configuration so the graft can be inserted into a blood vessel in a sheath or sleeve which slides along a guide wire inserted in the blood vessel.

If desired, the central portion 21 can be made from a material different than the material used to make the proximal portion 22 and/or distal portion 23. Portion 22 can be made of a material different from that of portions 21 and/or 23. Central portion 21 also need not be expandable and can, for example, be fabricated from dacron, nylon or some other synthetic material which has a diameter larger than the diameter of the proximal and distal portions 22, 23 and which is not expandable. Central portion 21 can be sutured or otherwise attached to the proximal portion 22 and/or distal portion 23. When, however, graft 20 is inserted in the body, the diameter of portion 21 is larger than the diameter of proximal and distal portions 22 and 23, and the diameter of portion 21 normally need not be increased after graft 20 is inserted in the body. Not having to increase the diameter of portion 21 after graft 20 is inserted in the body is an important advantage of the invention. After graft 20 is inserted in the body, the diameter of center portion 21 can, if desired, be increased with a balloon if portion 21 is made from an expandable material. Regardless of the materials utilized to fabricate graft 20, it is preferred, and important, that the graft can be folded or compressed and reduced to a size which facilitates insertion of the graft through a sheath into the desired blood vessel in the body.

As used herein, the term diameter refers to the outside diameter of the material used in the grafts of the invention. The grafts described herein consist of hollow cylindrical or substantially cylindrical portions. For example, central portion 21, proximal portion 22, and distal portion 23 are cylindrical hollow members.

Figure 2:
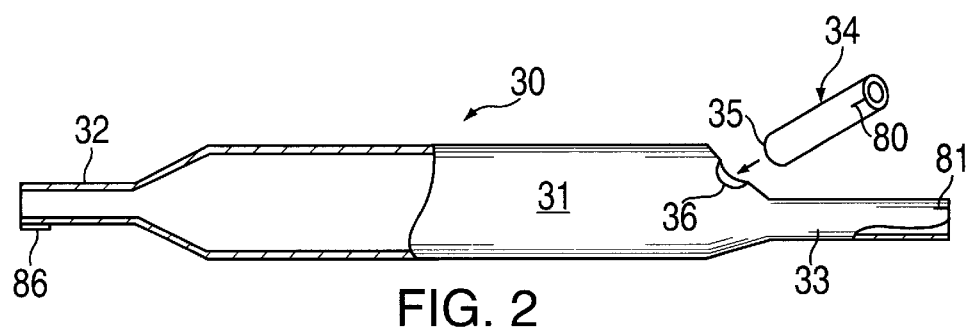
FIG. 2 is a side section view illustrating another embodiment of the blood vessel graft of the invention.

The graft 30 of FIG. 2 is, like graft 20, presently preferably made by taking a length of thin, pliable, foldable, hollow PTFE tubing and expanding an intermediate section to form center portion 31. Center portion 31 has a diameter greater than the proximal portion 32 and distal portion 33. The diameter of proximal portion 32 equals that of the original, unexpanded PTFE tubing, i.e. portion 32 comprises unexpanded PTFE tubing. The distal portion 33 is formed by expanding the PTFE tubing to a diameter which is greater than the diameter of portion 32 and less than the diameter of central portion 31. The diameter of distal portion 34 attached to opening 36 is also greater than the diameter of proximal portion 32 and is less than the diameter of center portion 31. Portion 34 is formed by expanding or pre-dilating hollow PTFE tubing. As discussed in connection with graft 20, portion 31 need not be made of an expandable material, can be made from a material different than that of portions 32 and 33, etc.

Figure 3:
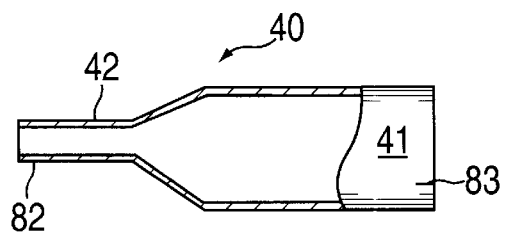
FIG. 3 is a side section view illustrating still another embodiment of the blood vessel graft of the invention.

The graft 40 of FIG. 3 is, like grafts 20 and 30, presently preferably made by taking a length of thin, pliable, foldable, hollow PTFE tubing and expanding an end section of the tubing to form portion 41. Portion 41 has a diameter greater than the proximal portion 42. As discussed in connection with graft 20, portion 41 need not be made of an expandable material, and can be made from a material different that of portion 42, etc.

The following examples are presented by way of illustration, and not limitation, of the practice of the invention.

EXAMPLE 1

The graft 20 of FIG. 1 is made by taking a length of two mm diameter PTFE tubing and expanding the center portion 21 to eight mm by introducing a balloon inside portion 21 and expanding the balloon with pressurized water. The diameter of proximal portion 22 is two mm. The diameter of distal portion 23 is two mm. The diameter of the pre-dilated center portion 21 in FIG. 1 is, as noted, eight mm. Radio opaque marker 84 is attached to proximal portion 22. Radio opaque marker 85 is attached to distal portion 23. Stents 24 and 27 are inserted in proximal portion 22 and distal portion 23, respectively. A balloon 25 is introduced in stent 24 and is expanded to about one atmosphere pressure to secure the balloon 25 in place inside stent 24 without causing stent 24 to expand. The balloon is carried on shaft 26. The graft 20—stents 24, 27—balloon 25—shaft 26 of FIG. 1 are tightly folded inside a sheath and inserted in a selected blood vessel about eight mm in diameter. Once the graft 20 is at the desired position in the blood vessel, balloon 25 is used to expand stent 24 and proximal portion 22 to about eight mm. After stent 24 is expanded, balloon 25 is deflated and moved to a position inside stent 27. Balloon 25 is expanded again to expand stent 27 and distal portion 23 to about eight mm.

EXAMPLE 2

The graft 40 of FIG. 3 is made by taking a length of five mm diameter expandable PTFE tubing and pre-expanding one end of the tubing to form the distal portion 41. Portion 41 has a diameter of 18 mm. The proximal portion 42 is not pre-expanded and has a diameter of five mm. A radiopaque marker 82 is affixed to the proximal portion 42. Another radiopaque marker 83 is affixed to distal portion 41. The distal portion 41 is long enough to span an aneurysm in the procedure described below in this Example 2. A balloon expandable aortic stent 43 is inserted in proximal end 42.

Figure 4:
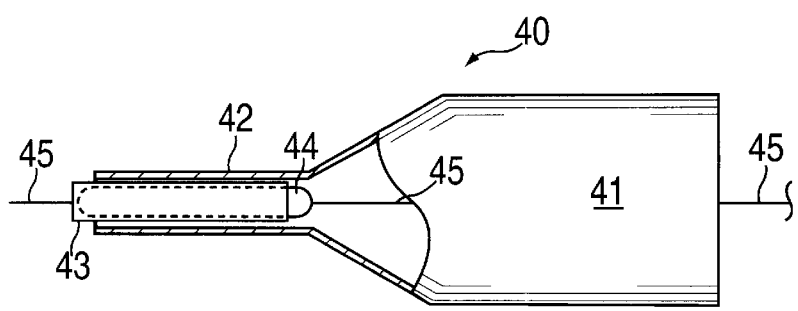
FIG. 4 is a side section view illustrating the graft of FIG. 3 provided with a stent and with an angioplasty balloon for securing the graft in position in a blood vessel.

A four cm long collapsed or folded angioplasty balloon 44 is inserted in stent 43 in the manner shown in FIG. 4 and inflated to two to three atmospheres to secure the balloon in stent 43 and proximal portion 42. Balloon 44 is carried on a guide wire 45. If the balloon is inflated standing alone outside of stent 43, it has an initial diameter of twenty cm after the balloon is filled sufficiently (to a pressure of about one atmosphere) to remove the folds from the balloon and assume a smooth arcuate configuration. As the pressure of water in the balloon is increased, the diameter of the balloon increases to its maximum labeled diameter.

In FIG. 4, the stent 43 is mounted in balloon 40 so that one end of stent 43 extends two mm outside the left hand end of proximal portion 42. If desired, stent 43 can be attached to proximal portion 42 with a single prolene suture or by any other desired means including a staple.

Figure 5:
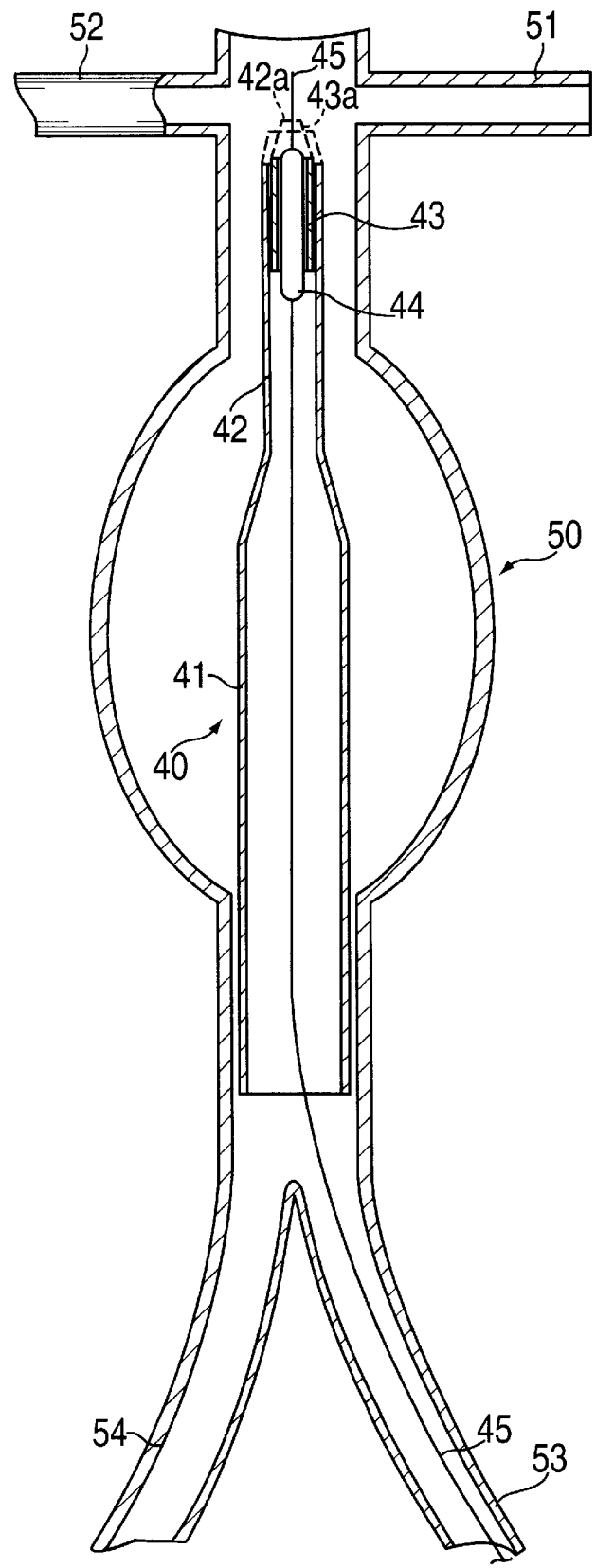
FIG. 5 is a side section view illustrating an aortic aneurysm with the graft of FIGS. 3 and 4 inserted therein.

After the balloon is inflated to two to three atmospheres in the configuration shown in FIG. 4, an eighteen Fr. French sheath is used to introduce the graft 40—stent 43—balloon 44 configuration through the common femoral artery percutaneously and to the level of the neck of the aneurysm 50 below the renal arteries 51 and 52 as shown in FIG. 5. The sheath is retracted or pulled along guide wire 45 to a position in the iliac artery 53. In FIG. 5, the end of proximal portion 42 is positioned in the proximal aneurysmal neck of the blood vessel. The end of distal portion 41 is positioned above the aortoiliac bifurcation.

In FIG. 5, the balloon 44 is expanded to expand stent 43 to force proximal portion 42 against the aneurysmal neck of the blood vessel and fix the graft 40 in place. Stent 43 and portion 42 are expanded to a diameter of about eighteen mm. Because of the high blood flow pressure through the aorta, a balloon is used to occlude the aorta from above while balloon 44 is expanded. Or, a steady pressure is applied to shaft 45 to hold balloon 44 in place during its inflation.

If desired, proximal portion 42 can include a tapered tip 42A and stent 43 can include a tapered tip 43A which are not expanded when balloon 44 is expanded in FIG. 5. In this case, after stent 43 and proximal portion 42 are expanded to the configuration shown in FIG. 6, then balloon 44 is deflated and moved upwardly in FIG. 5 into tapered tip 42A, where balloon 44 is again expanded to expand tip 43A and tip 42A to a diameter of about eighteen mm.

Figure 6:
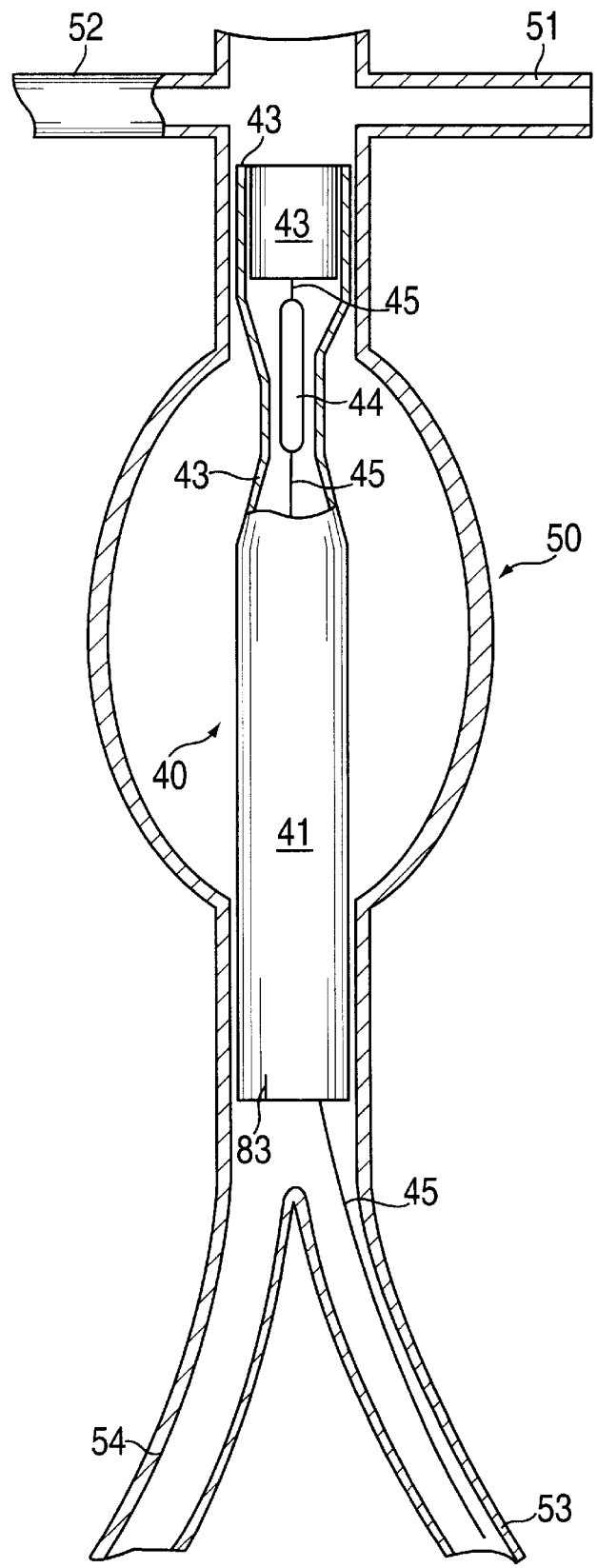
FIG. 6 is a side section view illustrating the aneurysm and graft of FIG. 5 after an angioplasty balloon is used to expand a stent and secure the graft in the aorta.

In FIG. 6, balloon 44 has been deflated and moved downwardly to a new position to expand the remaining unexpanded portion of proximal portion 43. After balloon 44 is in the position shown in FIG. 6, it is expanded to expand the constricted section of proximal portion 43 to about eighteen mm. The proximal portion 43 can be expanded to about eighteen mm because the balloon operator knows what balloon inflation pressure is required to expand the proximal portion 43 from five mm to eighteen mm and can view this procedure fluoroscopically.

Figure 7:
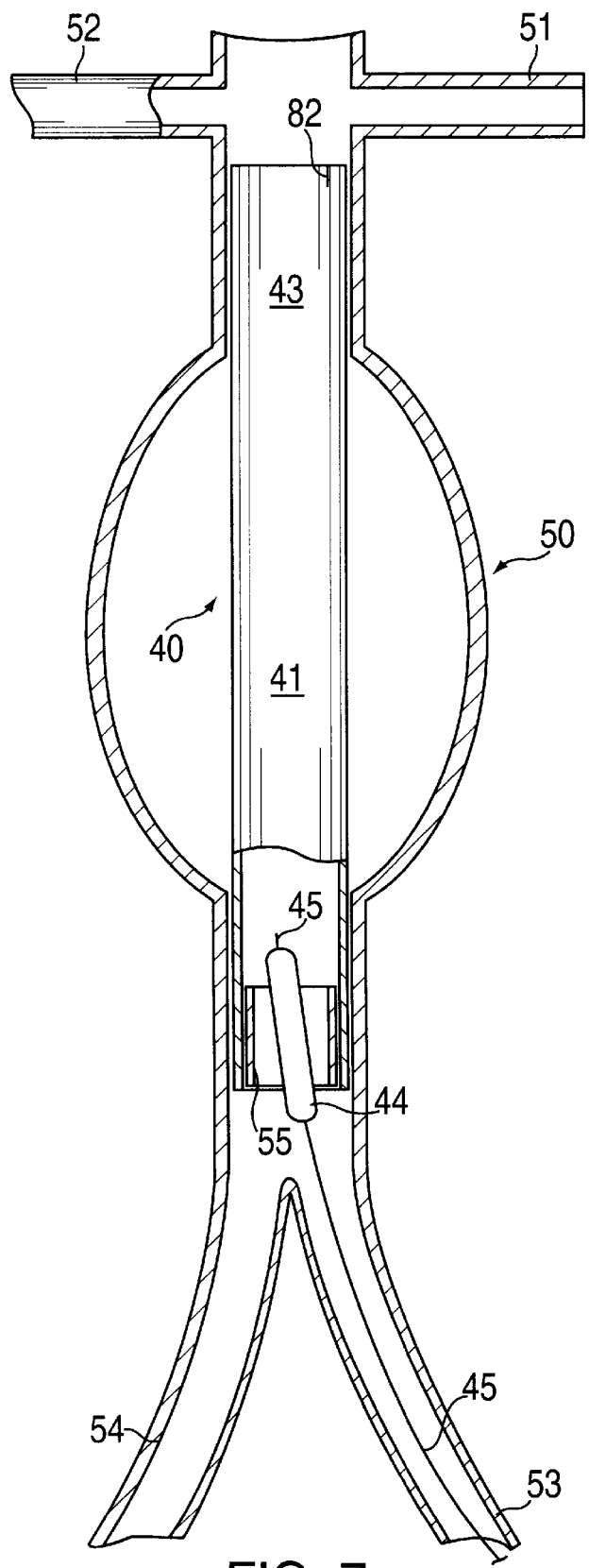
FIG. 7 is a side section view illustrating the aneurysm and graft of FIG. 6 after the proximal portion of the graft has been completely expanded.

Once proximal portion 43 is expanded to about eighteen mm along its entire length, balloon 44 is deflated and removed and, as shown in FIG. 7, an aortic stent 55 is deployed in the lower end of graft 40. A balloon 44 is used to expand stent 55 to force the lower end of distal portion 41 against the wall of the blood vessel. Balloon 44 is then deflated, and balloon 44 and shaft 45 are removed from the patient's body.

EXAMPLE 3

The graft 30 of FIG. 2 is made by taking a length of five mm diameter expandable PTFE tubing and pre-expanding an intermediate portion of the tubing to form the central portion 31. Portion 31 has a diameter of 20 mm. The proximal portion 32 is not pre-expanded and has a diameter of five mm. The first distal portion 33 is made by pre-dilating an end of the five mm tubing to nine mm with a nine mm angioplasty balloon catheter. Opening 36 is formed through graft 30 and the end 35 of a length 34 of pre-expanded PTFE is securely sutured around opening 36. The opening 36 is nine to ten mm wide and opens on the side of the graft. The anastomosis is from end to side. A size 4/0 PTFE, or similar material, continuous suture is used for the anastomosis. Length 34 comprises the second distal portion of the graft 30. Distal portion 34 is formed by pre-dilating a length of five mm diameter PTFE before portion 34 is sutured around opening 36. A radiopaque marker 81 is affixed to the outer end of distal portion 33. Another radiopaque marker 80 is affixed to the outer end of distal portion 34. A third radiopaque marker 86 is affixed to the outer end of proximal portion 32. If the graft 30 is being used to treat an aneurysm, the central portion 31 is long enough to span an aneurysm in the procedure described below in this Example 3. A balloon expandable aortic stent 43 is inserted in proximal end 42.

An aortic balloon expandable stent is inserted in the proximal end 32, followed by a twenty mm angioplasty balloon 65 (assuming the neck of the blood vessel above the aneurysm is about twenty mm in diameter). Balloon 65 is positioned inside stent 66. The wire 64 carrying balloon 65 extends from balloon 65 through center portion 31 and out through distal portion 34. The balloon 65 is inflated to a pressure of one to three atmospheres in order to fix the balloon and stent in graft 30. The one to three atmosphere pressure is less than the pressure needed to expand stent 66 and the proximal portion 32. The end of the proximal portion 32 is marked with a clip. The stent 66 can be secured to portion 32 with one or two single protene sutures.

Figure 8:
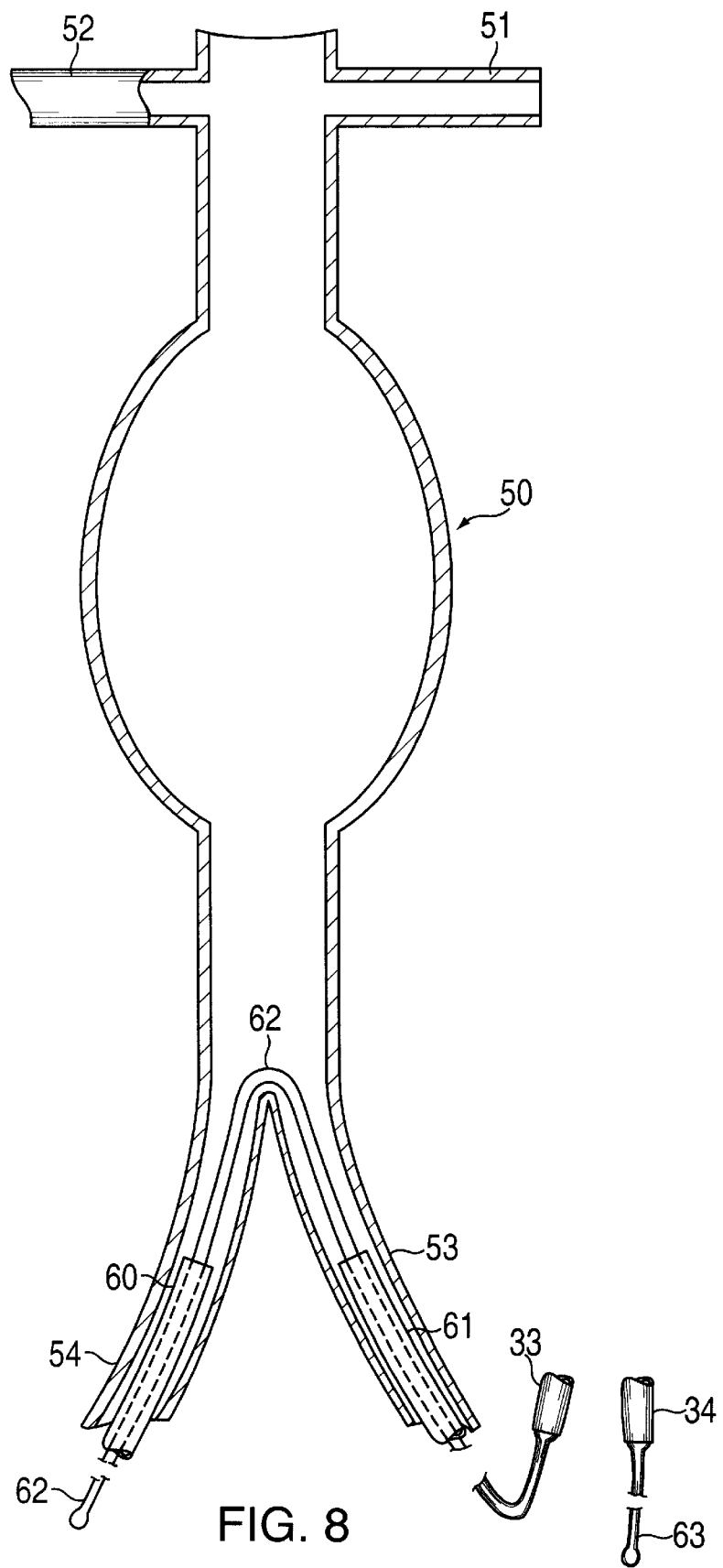
FIG. 8 is a side section view illustrating an aortic aneurysm after a suture loop has been coursed through the iliac arteries.

A loop 62 of prolene suture is introduced in a nine Fr. sheath 60 through the patient's right groin and is passed through iliac artery 54, through artery 53, through the eighteen Fr. sheath 61, and out through the patients left groin in the manner illustrated in FIG. 8. The end of loop 62 extending out of the patient's left groin is secured to the end of distal portion 33. Another loop 63 of suture is secured to the end of distal portion 34.

Figure 9:
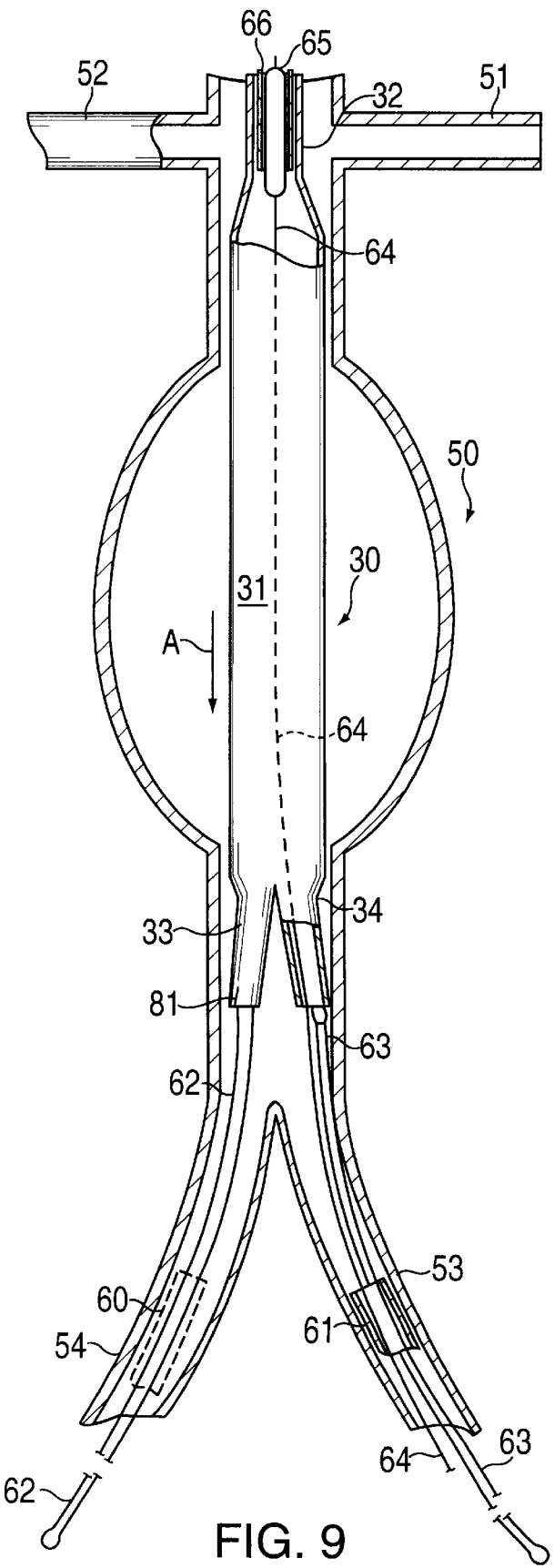
FIG. 9 is a side section view illustrating the aortic aneurysm of FIG. 8 after a split-leg graft has been inserted above the bifurcation of the aorta.

The graft 30—stent 66—balloon 65 is reduced or compressed into sheath 61 for the percutaneous introduction through artery 53 into the aorta of the patient. After graft 30 and sheath 61 are position in the aorta, sheath 61 is withdrawn into the iliac artery 53 and graft 30 is positioned in the aorta with distal portions 33 and 34 above the aortic bifurcation as shown in FIG. 9. As would be appreciated by those of skill in the art, radiopaque markers 80, 81, 86 permit the ready location of the graft 30 in the patient. In FIG. 9, loop 62 extends from distal portion 33 out through the right groin of the patient. Loop 63 extends from distal portion 34 out through the left groin of the patient.

Figure 10:
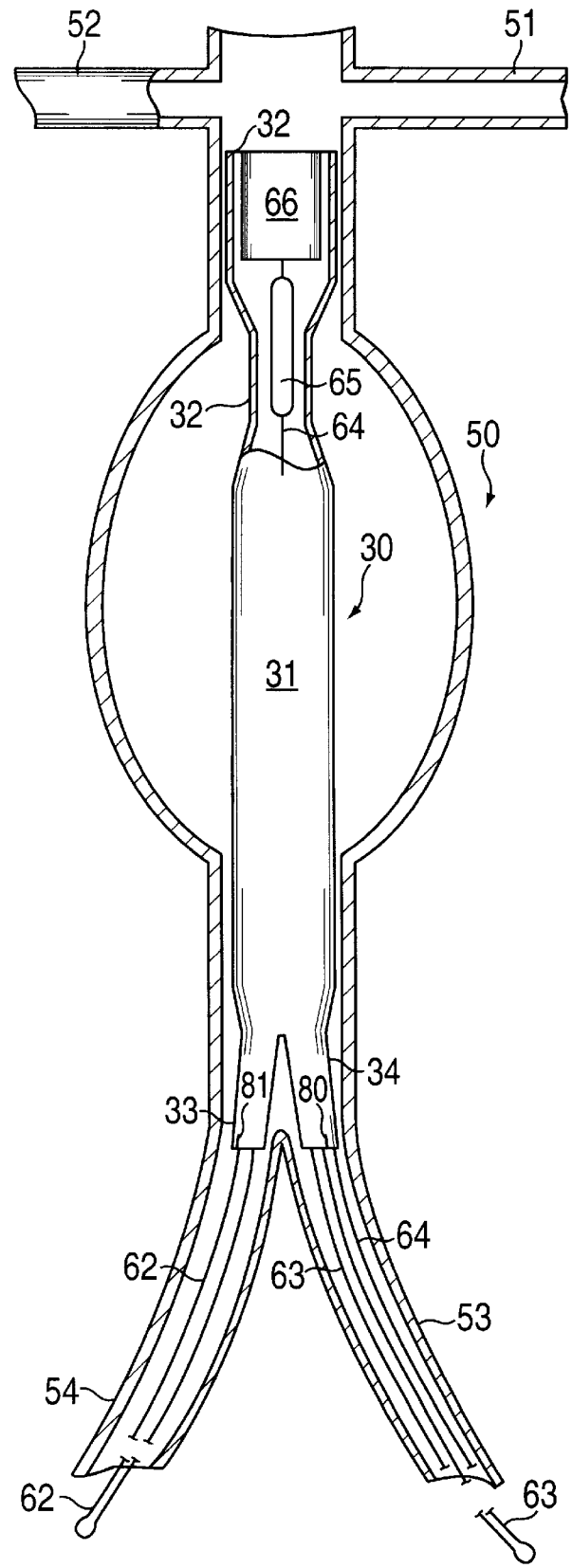
FIG. 10 is a side section view illustrating the aneurysm and graft of FIG. 9 after an angioplasty balloon is used to expand a stent in the aorta above the aneurysm to secure the graft in place; and, FIG. 11 is a side section view of the aneurysm and graft of FIG. 10 illustrating the insertion of a stent on one of the distal split legs of the graft to secure the graft in an iliac artery.

After graft 30 is in the position shown in FIG. 9, loops 62 and 63 are gently pulled to displace graft 30 in the direction of arrow A in FIG. 9 and to move distal portion 33 into artery 54 and distal portion 34 into artery 53 so that graft 30 assumes the general position illustrated in FIG. 10.

After graft 30 is in the general position shown in FIG. 10, balloon 65 is inflated to expand stent 66 and proximal end 32 to secure the graft in the aorta above aneurysm 50. FIG. 10 illustrates stent 66 and proximal portion 32 after balloon 65 has been inflated to expand stent 66 and after balloon 65 has then been deflated and moved downwardly into the remaining unexpanded portion of proximal portion 32. If possible, stent 66, portion 32, and/or balloon 65 can be sized such that after balloon 65 is inflated to expand stent 66, the entire length of portion 32 is expanded. In FIG. 10, portion 32 is expanded to a diameter approximately equal to the diameter of central portion 31.

After portion 32 is expanded and balloon 65 is deflated, the blood flow through the aorta helps to open distal portions 33 and 34.

Figure 11:
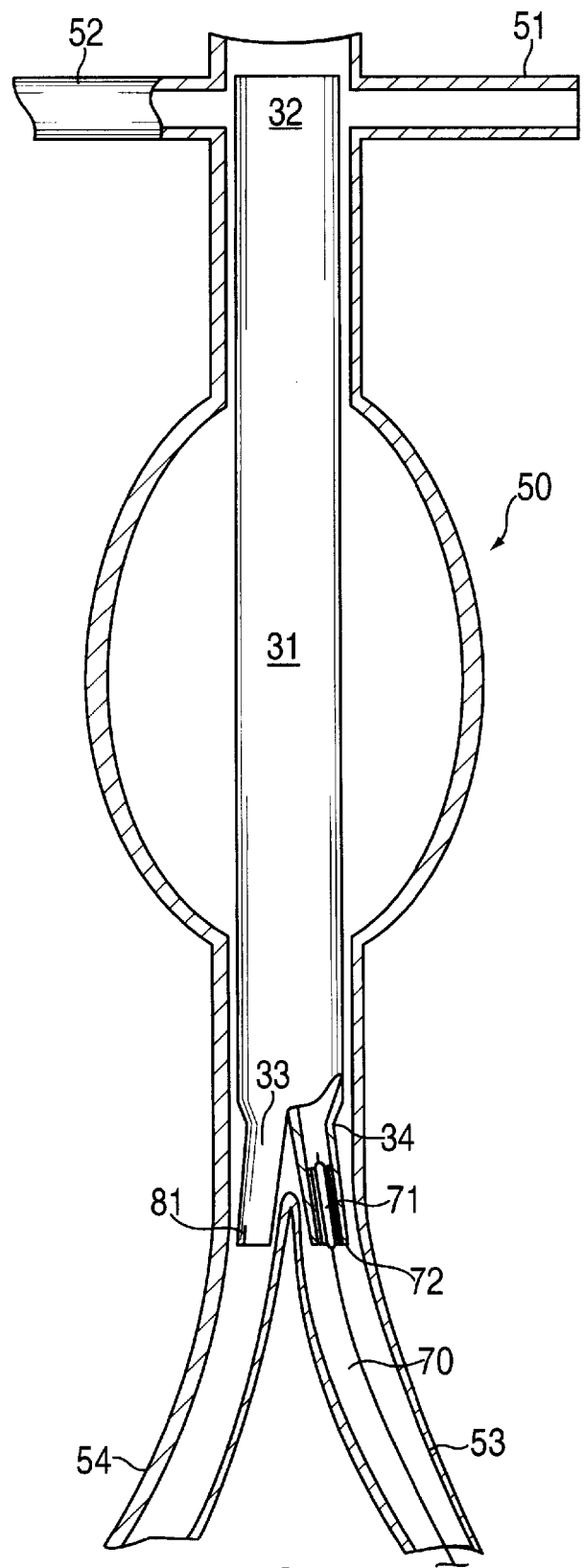

Balloon 65 and shaft 64 are removed from the patient. Loops 62 and 63 are removed. Stent 72 is inserted in distal portion 34 in the position shown in FIG. 11 and is expanded with balloon 71 on shaft 70 to secure portion 34 in artery 53. A similar stent is inserted in the lower end of distal portion 33 and is expanded to secure portion 33 in artery 54.

The expandable stents shown in FIGS. 1, 4 to 7, and 9 to 11 can be positioned inside a graft, outside of the graft, or intermediate layers of graft material when the graft is made from laminate cylindrical members. Many kinds of expandable stents are known in the art and will not be detailed herein. While it is possible that a self expanding stent could be utilized in the practice of the invention, it is presently preferred that balloon expandable stents be utilized to insure that the stents securely anchor a graft to a blood vessel.

Having described my invention in such terms as to enable those skilled in the art to understand and practice the invention, and having described the presently preferred embodiments thereof, I claim:

1. A method for positioning a graft at a desired site in a selected blood vessel, said method including the steps of:
   (a) providing said graft, said craft including:
      a first, larger diameter portion having a diameter corresponding substantially to the vessel inner diameter, said larger diameter portion being formed of a collapsable synthetic material; and
      a second, smaller diameter portion connected to said larger diameter portion and having a diameter that is less than the diameter of said larger diameter portion and the vessel inner diameter to facilitate insertion into the selected blood vessel, said smaller diameter portion being formed of an expandable synthetic material;
   (b) positioning an expansion element within said smaller diameter portion and collapsing said larger diameter portion to a reduced profile smaller than said vessel inner diameter,
   (c) inserting said graft and said expansion element in the selected blood vessel and locating said graft at the desired site; and
   (d) radially expanding said smaller diameter portion to the vessel inner diameter with said expansion element.

2. The method of claim 1 wherein said blood vessel has a diseased area defined by a diseased length, further comprising providing said draft with said larger diameter portion having a length that is longer than said diseased length and said smaller diameter portion is selected to engage a healthy portion of said selected blood vessel adjacent said diseased area.

3. The method of claim 1 comprising delivering said graft and expansion element over a guidewire.

4. The method of claim 1 comprising delivering said graft and expansion element through a sheath.

5. The method of claim 1 wherein said expansion element is an inflatable balloon and wherein said step of radially expanding includes inflating said inflatable balloon.

6. The method of claim 1, further comprising the steps of collapsing said expansion element and removing said expansion element from the blood vessel while leaving said graft in the blood vessel.

* * * * *